United States Patent [19]

Flaherty et al.

[11] Patent Number: 5,213,483

[45] Date of Patent: May 25, 1993

[54] PERISTALTIC INFUSION PUMP WITH REMOVABLE CASSETTE AND MECHANICALLY KEYED TUBE SET

[75] Inventors: J. Christopher Flaherty, Bedford; Francis P. Harrington, Beverly; William J. Gorman, Essex; Paul V. Fenton, Jr., Marblehead, all of Mass.

[73] Assignee: Strato Medical Corporation, Beverly, Mass.

[21] Appl. No.: 717,620

[22] Filed: Jun. 19, 1991

[51] Int. Cl.[5] .............................................. F04B 43/12
[52] U.S. Cl. ..................................... 417/477; 417/474; 604/153
[58] Field of Search ............... 417/474, 475, 476, 477; 604/153

[56] References Cited

U.S. PATENT DOCUMENTS

| | | | |
|---|---|---|---|
| 3,502,034 | 3/1970 | Pickup | 417/477 |
| 3,565,554 | 2/1971 | Muller | 417/477 |
| 3,791,777 | 2/1974 | Papoff | 417/477 |
| 3,927,955 | 12/1975 | Spinosa et al. | 417/477 |
| 3,990,444 | 11/1976 | Vial | 128/214 |
| 4,025,241 | 5/1977 | Clemens | 417/474 |
| 4,184,815 | 1/1980 | Casson et al. | 417/477 |
| 4,187,057 | 2/1980 | Xanthopoulos | 417/63 |
| 4,256,437 | 3/1981 | Brown . | |
| 4,273,121 | 6/1981 | Jassawalla | 128/214 |
| 4,303,376 | 12/1981 | Siekmann | 417/360 |
| 4,482,347 | 11/1984 | Borsanyi | 604/153 |
| 4,493,706 | 1/1985 | Borsanyi et al. | 604/153 |
| 4,537,561 | 8/1985 | Xanthopoulos | 417/63 |
| 4,557,725 | 12/1985 | Heyne et al. | 604/246 |
| 4,559,040 | 12/1985 | Horres et al. | 604/153 |
| 4,585,399 | 4/1986 | Baier | 417/477 |
| 4,657,490 | 4/1987 | Abbott | 417/478 |
| 4,671,792 | 6/1987 | Borsanyi | 604/153 |
| 4,673,334 | 6/1987 | Allington | 417/775 |
| 4,685,902 | 8/1987 | Edwards et al. | 604/153 |
| 4,758,238 | 7/1988 | Sundblom et al. | 604/319 |
| 4,790,829 | 12/1988 | Bowden et al. | 604/244 |
| 4,798,580 | 1/1989 | DeMeo et al. | 604/30 |
| 4,798,590 | 1/1989 | O'Leary | 417/477 |
| 4,818,186 | 4/1989 | Pastrone et al. | 417/63 |
| 4,850,807 | 7/1989 | Frantz | 417/63 |
| 4,886,431 | 12/1989 | Soderquist et al. | 417/477 |
| 5,074,756 | 12/1991 | Davis | 417/45 |

Primary Examiner—Richard A. Bertsch
Assistant Examiner—Peter Korytnyk
Attorney, Agent, or Firm—Lahive & Cockfield

[57] ABSTRACT

The system components include a peristaltic infusion pump device keyed for cooperation with a mutually keyed receiver which in turn is additionally keyed for receipt of a mutually keyed tube set having a selected fluid flow capacity for delivery of medical fluids at a selected fluid flow rate in a selected direction to or from a patient.

20 Claims, 3 Drawing Sheets

PERISTALTIC INFUSION PUMP WITH REMOVABLE CASSETTE AND MECHANICALLY KEYED TUBE SET

BACKGROUND OF THE INVENTION

The present invention relates to peristaltic infusion pumps for pumping of medical fluids and the like to and from a patient, and more particularly to a peristaltic infusion pump system which reduces the likelihood of incorrect connection and use between the system and a patient.

Peristaltic pumps of the type known for use for the infusion of medical fluids, or for the removal of body fluids from a patient, are generally characterized by use of a length of flexible tubing which is disposed within a compression chamber formed by a compression surface and a rotor assembly. The rotor assembly is typically provided with a Plurality of parallel axis rollers disposed about the periphery of a wheel-like rotor. Upon rotation of the rotor assembly, the rollers are biased against the tube which is supported by the compression surface, and the rollers successively pinch-off the tube and advance the location of the pinch-off so as to progressively advance the fluid within the tube at a rate in part determined by the angular acceleration and angular rate of rotation of the rotor. The pump rate is also determined by the viscosity of the fluid material, characteristics of the tubing through which the fluid flows, tube length and the inner and outer diameters of the tube through which the fluid flows. It is known to provide cassettes which facilitate the insertion and removal of such lengths of tubing into and out of the infusion pump. With such cassettes, typically, the user removes the cassette from the pump, and then positions the tube into the cassette (or within the housing of the pump) and then returns the cassette to the operating position. In some prior art configurations, the cassette includes the compression surface rigidly affixed to the cassette.

One danger of the prior art devices occurs because there is often a choice of tubes (of varying inner and outer diameters and other characteristics) which might be used so that a desired flow rate may be achieved. In such cases, operation error (in the selection of the tube) may lead to selection of the wrong diameter tube for the desired flow rate. Also in some cases, the direction of flow through the tube is important and it is possible for a user to install a tube backward, leading to deleterious results.

It is important to provide a peristaltic infusion pump in which fluid flow rate and fluid flow direction can be easily and accurately controlled. While present microprocessor and motor technologies enable provision of an intelligently controlled fluid pump, still prevention of user error is not guaranteed.

It is an object of the present invention to provide a peristaltic infusion pump system which reduces the likelihood of incorrect user hook-up and direction of operation.

It is another object of the present invention to provide a keyed removable cassette and a mutually keyed disposable tube set which dictates the direction of fluid flow and flow rate when utilized with a mutually keyed peristaltic infusion pump.

It is a further object of the present invention to provide a disposable tube set which is visually and tactilely keyed to directional fluid flow and flow rate in a mutually keyed receiver of a peristaltic infusion pump system.

SUMMARY OF THE INVENTION

The present invention provides a peristaltic infusion pump system for pumping of medical fluids and the like in a selected direction such as to or from a patient at a selected flow rate. The system is designed to reduce the likelihood of incorrect user selection of flow rate and flow direction by mechanically keying connection of the system integral components. Generally speaking, in one aspect of the invention, the system components include a peristaltic infusion pump device keyed for cooperation with a mutually keyed receiver which in turn is additionally keyed for receipt of a mutually keyed tube set having a selected fluid flow capacity for delivery of medical fluids at a selected fluid flow rate in a selected direction to or from a patient. The tube set includes a flexible tubular element with mechanically keyed portions adapted for interfitting with the receiver.

The receiver, which may be configured as an elongate cassette, is disposed for unidirectional receipt of a removable, unidirectionally keyed tube set having a selected fluid flow capacity, the tube set being of the type having a keyed input end which is structurally cooperable with a key structure of the receiver and a keyed output end which is structurally cooperable with another key structure of the receiver. Generally, the cassette includes a support for at least a portion of the flexible tubular element, and specifically includes a compression surface adapted for holding that portion of the tubular element against peristaltic drive rollers of the pump device. In the preferred form of the invention, the compression surface may establish a rigid surface that is floating (e.g. spring-biased) with respect to the cassette housing, so that the cassette housing may be removably attached to the pump device while permitting separate spring bias of the compression surface against a tube set positioned opposite the pump rollers. Alternatively, the compression surface may be rigidly affixed to the cassette housing.

In operation, the tube set is placed in its support in the receiver, with cooperatively keyed parts mating, and then the receiver-tube set combination is mounted on the pump device in the fluid flow path with the cooperatively keyed parts of the pump device and receiver being properly mated. Now, the fluid source is connected with a connector on the tube set input end, and a tube from the fluid target (i.e., the patient) is mated with the connector on the tube set output end.

In operation of the present pump system, the pump device establishes fluid flow in a predetermined fluid flow direction by having the tube set placed in the fluid flow path in a correct directional orientation by the receiver. A keyed tube set having a selected flow capacity is mated with a cooperatively keyed receiver, with the receiver in turn being cooperatively mated with the directionally keyed pump. A fluid input tube from a fluid source is coupled to the tube set input end and an input tube from a fluid delivery target is coupled to the tube set output end. With this configuration, fluid can be pumped at a selected flow rate in the assigned fluid flow direction within a fluid system, such as between a fluid source and a patient, without undue concern about the correctness of the fluid flow rate or flow direction.

Embodiments of the present invention therefore will be understood to include a directional tube set. Embodiments may also include a directionally keyed tube-set receiver, and a directionally keyed pump device. One embodiment of the invention includes a cooperating system of tube set, tube-set receiver and pump device.

BRIEF DESCRIPTION OF THE DRAWINGS

These and other features and advantages of the present invention will be more fully understood by reference to the following detailed description in conjunction with the attached drawing in which like reference numerals refer to like elements and in which.

DETAILED DESCRIPTION OF PREFERRED EMBODIMENTS

Figure 1:
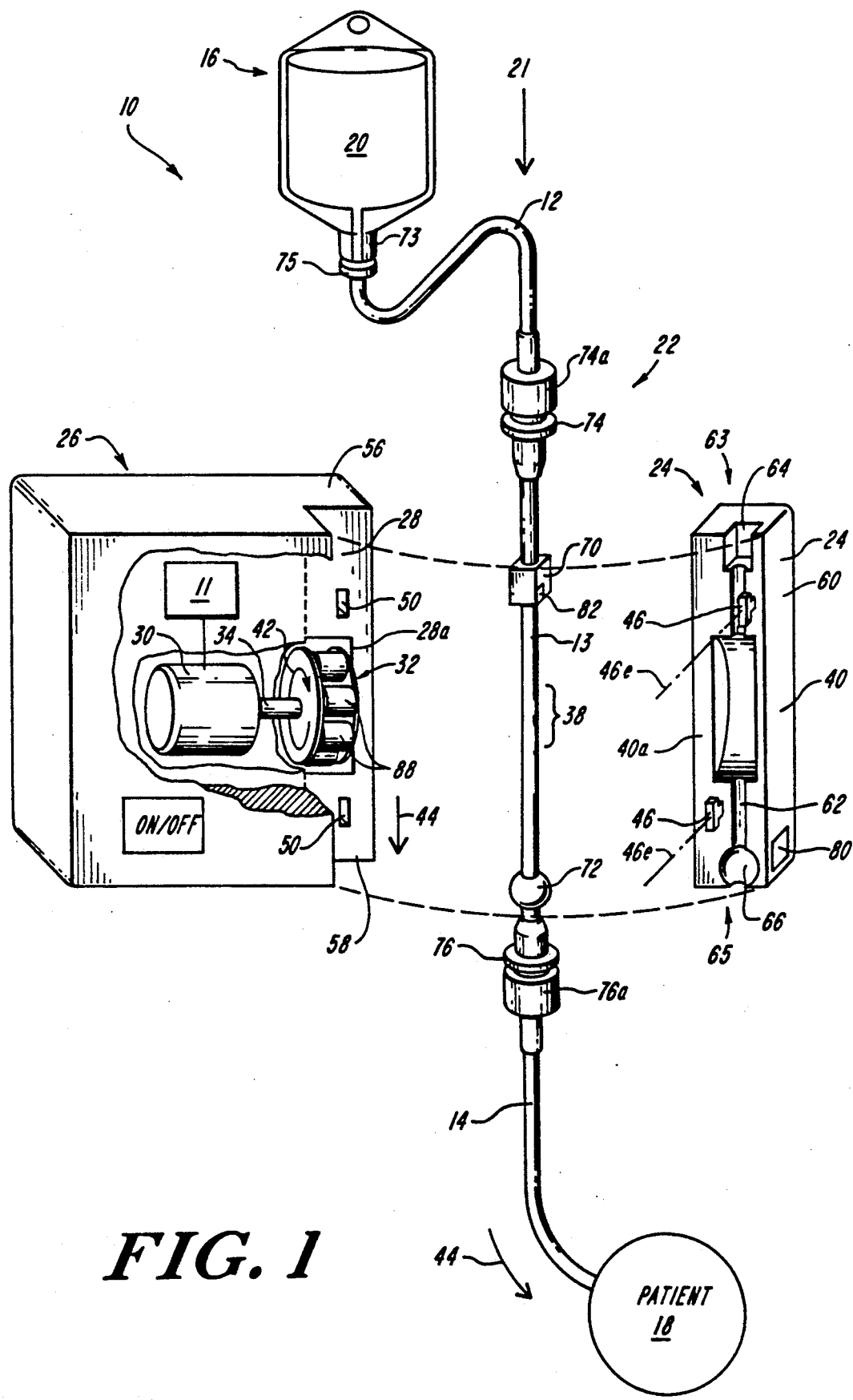
FIG. 1 is an exploded schematic view of an illustrative embodiment of the present invention for delivery of fluid from a source to a patient.

FIG. 1 is a partially exploded schematic representation of a peristaltic infusion pump system 10 in practice of the present invention. System 10 is coupled by tubes 12, 13, and 14 of a directionally keyed tube assembly 21 between a medicinal fluid source 16 and a patient 18 for delivery of fluid 20 from source 16 to patient 18, for example. Tube 13 itself is part of a tube set 22 which mates with a directionally keyed cassette-type receiver 24, which in turn mates against a substantially planar coupling surface 28 of a cooperatively directionally keyed peristaltic pump device 26.

Pump device 26 includes a motor 30 which drives a generally cylindrical fluid flow directional device 32, such as a cammed rotor 32, mounted on the shaft 34 of motor 30. The cammed rotor 32 includes a plurality of peripherally located rollers. Rotor 32 is positioned with its axis of rotation substantially parallel to the plane of surface 28 and within the housing of device 26 so that a portion 32a of the cammed rotor 32 extends through an aperture 28a of substantially planar coupling surface 28. In this context, the portion 32a of the rotor 32 that extends beyond the plane of the coupling surface 28 is referred to as the "chordal" portion.

Figure 2:
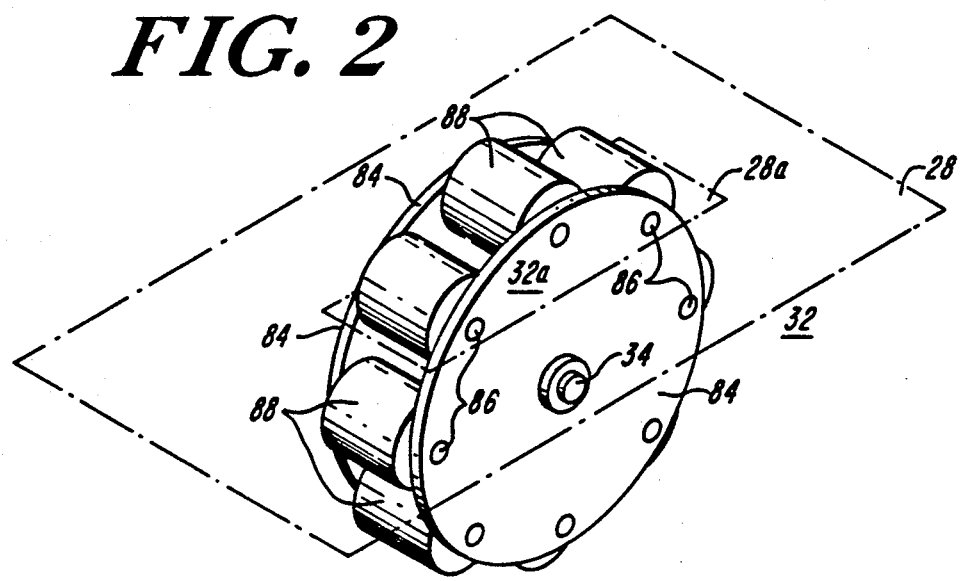
FIG. 2 is a perspective view of a preferred pump rotor assembly.

The motor 30 is disposed for rotation in a selected or prescribed direction 42 so as to generate fluid flow in a direction 44 along a directionally keyed fluid flow path from fluid source 16 to the patient 18. Pump device 26 operates under the control of processor 11. A preferred embodiment of cammed rotor 32 is shown in FIG. 2 including a pair of circular rotor plates 84 which are coupled at their centers to the motor shaft 34 and are also mated by axial pins 86 mounted along the periphery of the plates. A respective roller 88 is rotatably mounted on a respective pin 86. Each roller 88 forms a cam for pumping interaction with the tube assembly tube 13 against a compression surface 40 (described below) when the tube is appropriately mounted in the fluid flow path.

With tube set 22 mounted in receiver 24, which in turn is mounted in pump device 26, the rotating cams 88 of rotor 32 engage a section 38 of tube 13 of the tube set and closes it off to fluid flow by forcing section 38 against a compression surface 40 of receiver 24, and then by continued rotation of the cam about its principal axis, fluid 20 advances in the tube in the direction 44. This establishes an input or inflow end 56 and an output or outflow end 58 of the pump device 26.

Figure 3A:
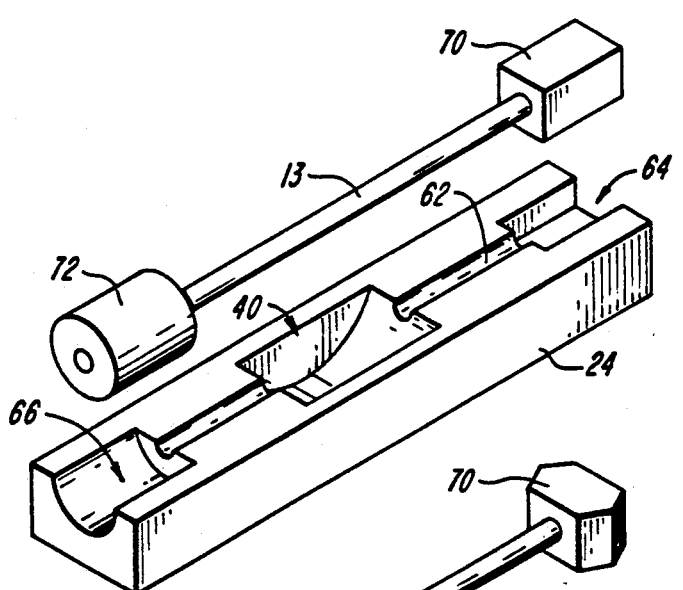
FIGS. 3A and 3B illustrate two different cassettes and associated tube sets in accordance with the invention.
Figure 3B:
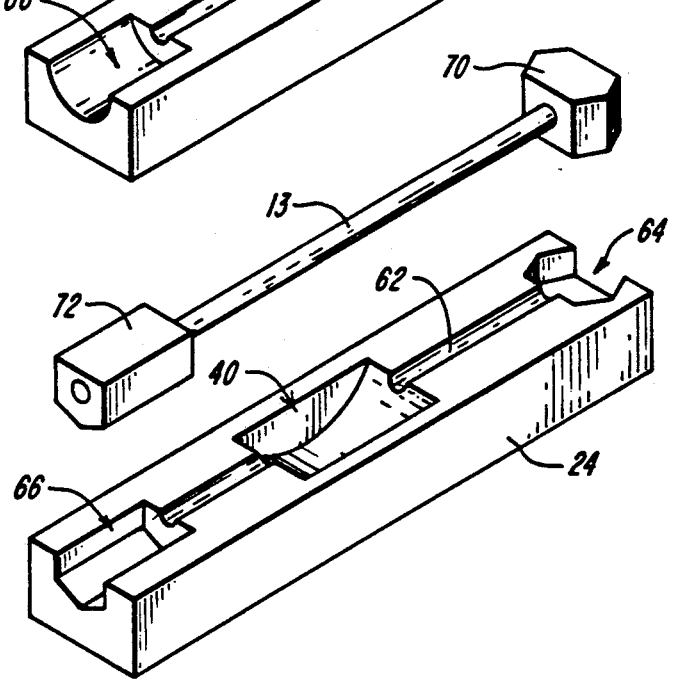

Receiver 24 is essentially an elongate cassette having a receiver surface 60 which defines compression surface 40. In the preferred form of the invention, the compression surface 40 is established by compression member 40a which is captively and resiliently held within, and spring-biased away from, the housing 24a of receiver 24. In other embodiments, the surface may be rigidly affixed to the receiver 24 (e.g. as shown in FIGS. 3A and 3B). Receiver 24 also includes a channel 62 which terminates at a respective input keyway 64 on an input end 63 of the receiver and an outlet keyway 66 on an output end 65 of the receiver. Keyways 64 and 66 are dissimilarly configured, which provide a method for distinguishing between the input and output ends of the receiver and of an associated tube set 22. The receiver is further provided with spring-biased latch elements 46 which extend along axes 46e out from surface 60. One or several latch receivers, such as cavities positioned behind rectangular apertures 50, are provided on pump device 26 for receipt of the cooperating latches 46 of receiver 24. To engage a cassette to device 26, the receiver 24 is initially positioned so that latch elements 46 are angularly oriented as illustrated and extend through apertures 50 into the cavities. Then, the latch elements 46 are rotated 90 degrees about axes 46e so that they are captured within the cavities. As a result of mechanical keying, the receiver can be mounted in fluid flow path 28 in only one orientation, i.e., establishing fluid flow in direction 44 from the fluid source 16 to the patient target 18. The latch portion of receiver 24 is described below in conjunction with FIG. 4.

Tube 13 has connectors at each end; connector 74 is at the inflow end and connector 76 is at the outflow end. Tube 13 also has a key element at each end; key element 70 is at the inflow end and key element 72 is at the outflow end. The key elements 70 and 72 are coordinated so as to assure the correct direction of fluid flow into the patient, for example. Tube 12 of tube assembly 22 includes a conventional connector 75 (such as a Luer connector) for threaded engagement with a mating connector 73 of fluid source 16 (e.g., an I.V. bottle) and also includes a connector 74a adapted to mate with connector 74 of tube 13. Tube 14 includes a connector 76a adapted for connection to connector 76 of tube 13. In the illustrated embodiment, connector 74 and key element 70 are discrete structures as are connector 76 and key element 72, but in other embodiments the respective connectors and key elements may be integral structures.

Keyblocks 70, 72 are dissimilarly configured, which provides a tactile as well as visual manner of distinguishing between the input and output ends of the tubes. Hence, only correct connection of the input connector 74 with a source 16 and output connector 76 with a patient 18 can be made.

The key element 70 is externally configured to have a specific shape, such as a cube or other polyhedral shape, for example, to indicate the input end of tube set 22. Key element 70 mates with cooperatively configured keyway 64 of receiver 24. Meanwhile, the key element 72 of tube set 22 is also externally configured to have a specific shape (different from the shape of key element 70), such as spherical. Thus key element 72 is externally configured to have a shape which is inconsistent with the configuration of key element 70, so as to further provide indication of intended direction of fluid flow. Element 72 mates with the cooperatively configured keyway 66 of receiver 24. Hence, tube set 22, and in fact the entire tube assembly 21, can mate and interact with the receiver 24 and pump 26 only consistent with fluid flow direction 44.

The present embodiment is particularly adapted to use disposable tubes 13 which may be readily connected to conventional tubes (like tubes 12 and 14) to rapidly configure an I.V. system. The tubes 13 may also be selected to provide flow rate control by using tubes with selected inner diameters.

It will now be appreciated that assuring the proper directionality of system 10, i.e., assuring intended fluid flow from source 16 to patient 18, with the pump device 26 already having established pumping direction 44, is provided by the interaction of the respective mutual keyings between the pump device 26 and the receiver 24, between the receiver 24 and the tube assembly 22, and may also be provided between the connectors of the tube assembly 22 and of the respective input and output tubes 12, 14.

Flow rate may be controlled in part by controlling the rate of rotation of the rotor cam 33. This requires control circuits, and also some degree of skill on the part of the user. Therefore, for simplicity of construction and use, a d.c. (constant rate) motor (as opposed to a variable speed motor) is preferred, although some amount of pump angular displacement control may also be provided. Processor 11 is coupled to motor 30 and enables the user to select a desired pumping regimen, e.g., for periodic infusions or infusion based upon an externally generated signal input, and also for programming fluid flow rate.

In accordance with a preferred embodiment of the present invention, flow rate is conveniently controlled by selection of a tube set 22 with a desired fluid flow capacity. Such fluid flow capacity is substantially determined by the internal and outer diameters and elasticity of tube 13, although other tube characteristics also do contribute to flow capacity. Preferably, each tube set has a selected internal diameter which is associated with a unique combination of external configurations of key element 70 and key element 72 and an associated configuration of respective receiver keyways 64, 66, which in turn is associated with a designated fluid flow rate. By way of example, a first flow rate cassette may include cubic and spherical keyways 64 and 66, respectively, while a second flow rate cassette may include corresponding keyways that are tetrahedrons and cylinders, for example. Correspondingly keyed tube sets would only fit in the associated cassette, thereby eliminating the chance of user error.

In alternative embodiments, the key elements (and keyways) may be identical at both ends of tube set 22 (and cassette 24), for example, where directionality is not important, but where the shape corresponds to a particular inner diameter of tube 13.

FIGS. 3A and 3B illustrate two exemplary cassettes 24 and associated tube sets 13, where the keyways are different for each cassette. The tube sets may be further provided with a respective connector at key elements 70, 72 for connection with a respective connector of input/output tubes 12, 14.

In one form of the invention, tube 13 is provided with a unique external diameter relative to its flow rate. Now, in order to ensure a user's selection of the correct flow rate, each cassette is provided with a marking 80, and each cooperating tube set 22 is optionally provided with a marking 82, each of which indicates an assigned fluid flow rate. Furthermore, receiver channel 62 is adapted to the appropriate external diameter of tube 13 according to an assigned fluid flow rate to assure correct compression of the tub against the receiver compression surface 40.

The simple selection of an appropriately marked cassette according to marking 80 and selection of an appropriately sized tube set 22 according its cooperation with keyways 64, 66 (and perhaps also according to optional marking 82) is all that is required to set flow rate. Thus, with a fixed pump rate, it is relatively simple, in accordance with the invention, to adjust flow rate without error in rate or direction of flow by selection of an appropriately marked, keyed combination of cassette and tube set.

The tube set 22 is nominally shorter in length than the separation between receiver keyways 64, 66 by an amount such that the tube set must be stretched and will be held under tension when it is installed in receiver 24. This assures accurate presentation of the tube set tube 13 to pump device 26 and also minimizes tube creep caused by the rotational engagement of the rotating pump cam (such as the rollers 88) and tube 13 against compression surface 40 of the cassette.

In operation of the present pump system, the pump device 26 establishes fluid flow in the assigned fluid flow direction 44 by the receiver's placing tube set 22 in the fluid flow path in a correct directional orientation according to the keyways 64, 66 of the receiver and the cooperating configuration of tube set key element 70 and key element 72. That is, a keyed tube set having a selected flow capacity is mated with a cooperatively keyed receiver, with the receiver in turn being cooperatively mated with the directionally keyed pump. A keyed fluid input tube from a fluid source is coupled to the tube set keyed input end and a keyed output tube from a fluid delivery target (such as a patient) is coupled to the tube set keyed output end. Then, fluid may be pumped at a selected flow rate in the assigned fluid flow direction within a fluid system, such as between a fluid source and a patient, without undue concern about the correctness of the flow rate or flow direction. An additional advantage of the present invention is that the pump and receivers are reusable, while only the relatively inexpensive, contaminated tube sets themselves need be disposable.

The pump device housing and the receiver may be made from metal or hard plastic, for example. The tube assembly tubes 12 and 13 are preferably made from conventional materials. The connectors and keying element of the tube assembly can be made from various conventional materials.

Figure 4:
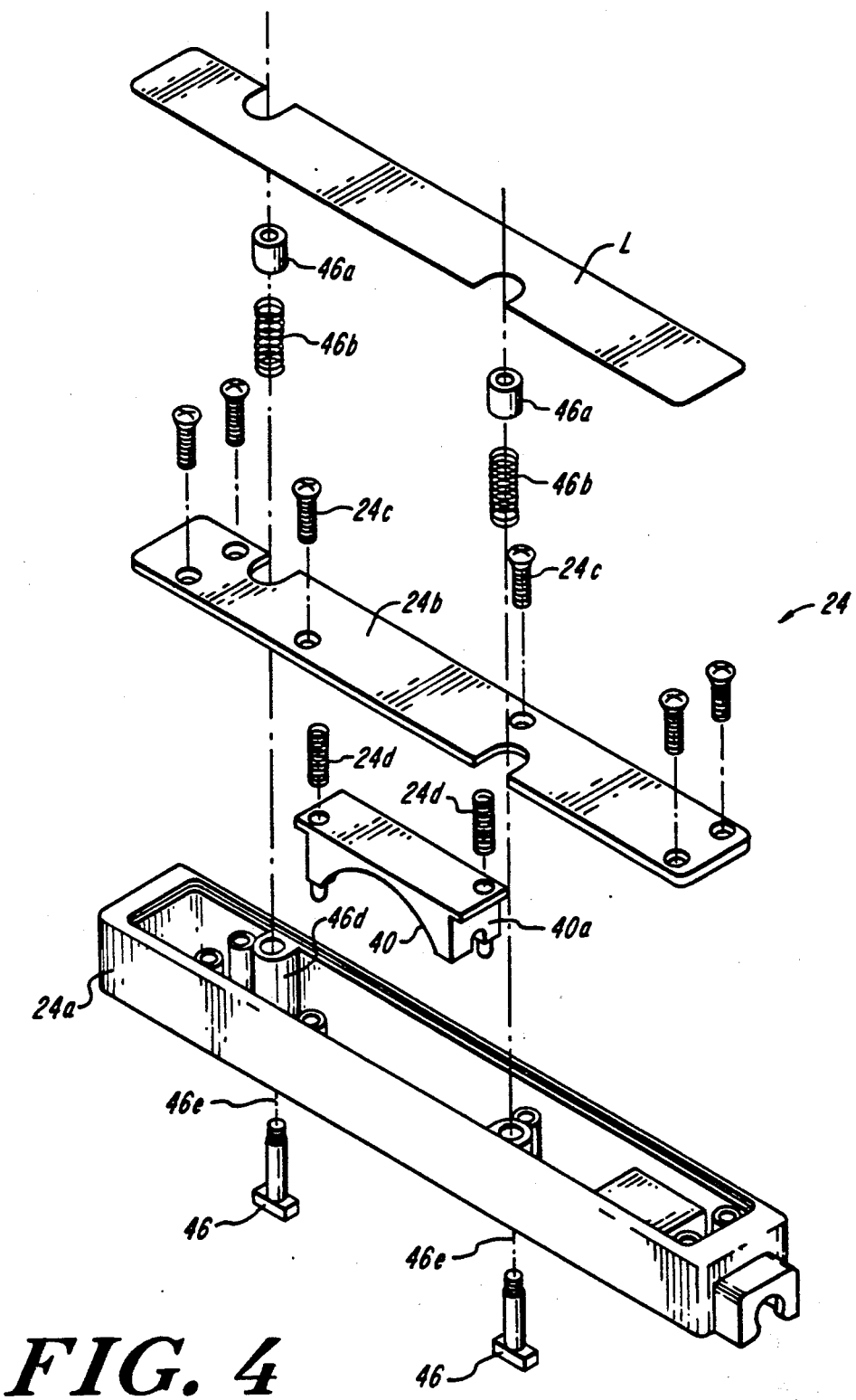
FIG. 4 is an exploded schematic view of a preferred form of the cassette (receiver) of the embodiment of FIG. 1.

In the preferred form of the invention, receiver 24 has the general form shown in FIG. 4. In that form, the receiver housing 24a and a back panel 24b captively house a saddle element 40a bearing the compression surface 40. The element 40a is spring-biased to the back panel 24b by way of screws 24c and associated springs 24d, so that the compression surface "floats" with respect to the receiver housing 24a. The latch elements 46 of receiver 24 are affixed at their distal ends to stop members 46a and are spring loaded (via springs 46b), friction fit housings 46c, so that the latch elements may selectively be rotated about axes 46e, as desired, to lock the receiver 24 to the pump 26. A label L is positioned on the back panel 24b for receiving indicia indicative of certain operation instructions, or for identification purposes.

While the invention has been described in the form of embodiments having directional keying as well as flow rate keying, various embodiments may incorporate only one of these aspects of the invention. For example, flow rate control may be accomplished with tube sets having identical key elements at both ends, making no difference which direction is used in insertion into the cassette.

The above description pertains to only several embodiments of the present invention. That is, the description is provided by way of illustration and not by way of limitation. The invention, therefore, is to be defined according to the following claims.

What is claimed is:

1. A plurality of tube sets, each tube set being for insertion into a respective one of a corresponding plurality of removable cassettes of a peristaltic pump system, said cassettes each having mechanical keying to indicate a unique demand rate of fluid flow, each tube set comprising:
   a flexible tubular element, and
   key means attached to said tubular element for mechanically coupling said tube set to its corresponding cassette, said tube set being adapted for cooperatively interfitting with said mechanical keying only of a cassette having its corresponding unique demand rate of fluid flow.

2. The tube set of claim 1 wherein the tube set comprises a tube having a first key element at one end and a second key element at the other end, each key element being configured to mechanically cooperatively interfit with a respective keying in said cooperating cassette.

3. The tube set of claim 2 wherein said first key element and said second key element having substantially the same exterior shape whereby either key element may cooperatively interfit with either keying in said cassette.

4. The tube set of claim 3 wherein the inner diameter of said tubular element is substantially determinative of the maximum fluid flow rate through said tubular element.

5. The tube set of claim 2 wherein said first key element and said second key element have different exterior shapes whereby each key element may only cooperatively interfit with only one of said keying of said cassette.

6. The tube set of claim 4 wherein the inner diameter of said tubular element is substantially determinative of the maximum fluid flow rate through said tubular element.

7. A plurality tube sets, each tube set being for insertion into a respective one of a corresponding plurality of removable cassettes of a peristaltic pump system, said cassettes each having mechanical keying to indicate a unique demand rate of fluid flow, and at least one of said cassettes having mechanical keying to indicate a predetermined demand direction of fluid flow, each tube set comprising:
   a flexible tubular element,
   key means for mechanically coupling said tube set to said cassette, said tube set being adapted for cooperative interfitting with said mechanical keying only of a cassette having its corresponding unique rate of fluid flow, and
   said tube set corresponding to said one cassette further comprising:
   key means for mechanically coupling said tube set to said cassette, said directionality key means being adapted for cooperatively interfitting only with said mechanical keying of said one cassette such that the direction of the tube set fluid flow when the tube set is mounted in said cassette is only aligned along said predetermined demand direction of fluid flow.

8. The tube set of claim 7 wherein the tube set comprises a tube having a first key element at one end and a second key element at the other end, each key element being configured to mechanically cooperatively interfit with a respective keying in said cooperating cassette.

9. The tube set of claim 8 wherein said first key element and said second key element having substantially the same exterior shape whereby either key element may cooperatively interfit with either keying in said cassette.

10. The tube set of claim 8 wherein said first key element and said second key element have different exterior shapes whereby each key element may only cooperatively interfit with only one of said keying of said cassette.

11. A peristaltic infusion pump system including a pump device having an input end and an output end, the pump device being adapted for pumping of fluids from said input end to said output end at a selected flow rate, said system comprising:
   A. a plurality of tube sets, each set having a flexible, elongated tubular element extending between a first rigid key element at a first end thereof and a rigid second key element at a second end thereof, wherein said key elements of each tube set are collectively indicative of a unique predetermined flow capacity for said tube set and are characterized by a unique associated shape,
   B. a plurality of detachable tube set receivers, each detachable tube set receiver being uniquely associated with one of said tube sets, and including means for mating with a support member of said pump device, each of said tube set receivers including a compression member having a compression surface and including support means for supporting said key elements of its associated tube set with at least a portion of said tubular element opposite said compression surface and said support means including keyway means for cooperatively interfitting only said key elements of said associated tube set,,
   C. A circular rotor including a plurality of rollers disposed about the rotor periphery, said rotor adapted for rotation about a first axis, said rollers being adapted for rotation about respective axes parallel to said first axis,
   D. means for removably coupling said tube set receiver to said support member whereby said rollers are successively adjacent to said compression surface as said rotor rotates about said first axis, and
   E. means for selectively driving said rotor to rotate about said first axis,.

12. The system of claim 11 wherein said first key element and said second key element have substantially the same exterior shape whereby either key element may cooperatively interfit with either key way in said receiver.

13. The system of claim 12 wherein the inner diameter of said tubular element is substantially determinative of the maximum fluid flow rate through said tubular element.

14. The system of claim 11 wherein said first key element and said second key element have different exterior shapes whereby each key element may only cooperatively interfit with only one of said key way of said receiver.

15. The system of claim 14 wherein the inner diameter of said tubular element is substantially determinative of the maximum fluid flow rate through said tubular element.

16. The system of claim 11 wherein said key elements and said keyways are indicative of a predetermined demand direction of fluid flow.

17. The system of claim 16 wherein said first key element and said second key element have substantially the same exterior shape whereby either key element may cooperatively interfit with either keying in said receiver.

18. The system of claim 16 wherein said first key element and said second key element have different exterior shapes whereby each key element may only cooperatively interfit with only one of said keying of said receiver.

19. The system of claim 11 wherein said coupling member is resiliently coupled to said support means.

20. The system of claim 19 wherein said coupling member is coupled to said support means by a plurality of springs.

* * * * *